US008524773B2

(12) United States Patent
Joshi et al.

(10) Patent No.: US 8,524,773 B2
(45) Date of Patent: *Sep. 3, 2013

(54) UTILIZATION OF DIALKYLFUMARATES

(75) Inventors: Rajendra Kumar Joshi, Zürich (CH); Hans-Peter Strebel, Muri (CH)

(73) Assignee: Biogen Idec International GmbH, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/612,221

(22) Filed: Sep. 12, 2012

(65) Prior Publication Data

US 2013/0004526 A1 Jan. 3, 2013

Related U.S. Application Data

(60) Division of application No. 13/040,914, filed on Mar. 4, 2011, which is a continuation of application No. 12/405,665, filed on Mar. 17, 2009, now Pat. No. 7,915,310, which is a continuation of application No. 11/765,578, filed on Jun. 20, 2007, now Pat. No. 7,619,001, which is a continuation of application No. 10/197,077, filed on Jul. 17, 2002, now Pat. No. 7,320,999, which is a division of application No. 09/831,620, filed as application No. PCT/EP99/08215 on Oct. 29, 1999, now Pat. No. 6,509,376.

(30) Foreign Application Priority Data

Nov. 19, 1998 (DE) .................. 198 53 487

(51) Int. Cl.
 *A61K 31/225* (2006.01)
(52) U.S. Cl.
 USPC .......................... 514/547; 514/903
(58) Field of Classification Search
 USPC ................ 514/547, 903
 See application file for complete search history.

(56) References Cited

U.S. PATENT DOCUMENTS

| 3,832,287 | A | 8/1974 | Gale et al. |
|---|---|---|---|
| 4,515,974 | A | 5/1985 | Zecher et al. |
| 4,746,668 | A | 5/1988 | Sato et al. |
| 4,851,439 | A | 7/1989 | Speiser et al. |
| 4,894,366 | A | 1/1990 | Okuhara et al. |
| 4,959,389 | A | 9/1990 | Speiser et al. |
| 5,149,695 | A | 9/1992 | Speiser et al. |
| 5,214,196 | A | 5/1993 | Blank |
| 5,242,905 | A | 9/1993 | Blank |
| 5,359,128 | A | 10/1994 | Blank |
| 5,424,332 | A | 6/1995 | Speiser et al. |
| 5,451,667 | A | 9/1995 | Speiser et al. |
| 5,538,968 | A | 7/1996 | Chiesi et al. |
| 5,548,059 | A | 8/1996 | Bayley et al. |
| 5,589,504 | A | 12/1996 | Dannenberg et al. |
| 5,650,492 | A | 7/1997 | Gately et al. |
| 5,972,363 | A | 10/1999 | Clikeman et al. |
| 6,087,540 | A | 7/2000 | Kamigauchi et al. |
| 6,277,882 | B1 | 8/2001 | Joshi et al. |
| 6,355,676 | B1 | 3/2002 | Joshi et al. |
| 6,359,003 | B1 | 3/2002 | Joshi et al. |
| 6,436,992 | B1 * | 8/2002 | Joshi et al. ............ 514/547 |
| 6,509,376 | B1 | 1/2003 | Joshi et al. |
| 6,858,750 | B2 | 2/2005 | Joshi et al. |
| 7,157,423 | B2 | 1/2007 | Joshi et al. |
| 7,320,999 | B2 * | 1/2008 | Joshi et al. ............ 514/549 |
| 7,432,240 | B2 | 10/2008 | Joshi et al. |
| 7,612,110 | B2 | 11/2009 | Joshi et al. |
| 7,619,001 | B2 * | 11/2009 | Joshi et al. ............ 514/547 |
| 7,790,916 | B2 | 9/2010 | Joshi et al. |
| 7,795,310 | B2 | 9/2010 | Lee et al. |
| 7,803,840 | B2 * | 9/2010 | Joshi et al. ............ 514/547 |
| 7,906,659 | B2 | 3/2011 | Joshi et al. |
| 7,915,310 | B2 | 3/2011 | Joshi et al. |
| 8,067,467 | B2 | 11/2011 | Kumar et al. |
| 2003/0013761 | A1 | 1/2003 | Joshi et al. |
| 2003/0018072 | A1 | 1/2003 | Joshi et al. |
| 2004/0038889 | A1 | 2/2004 | Joshi et al. |
| 2004/0054001 | A1 | 3/2004 | Joshi et al. |
| 2005/0148664 | A1 | 7/2005 | Joshi et al. |
| 2006/0069161 | A1 | 3/2006 | Lee et al. |
| 2006/0205659 | A1 | 9/2006 | Joshi et al. |
| 2007/0027076 | A1 | 2/2007 | Joshi et al. |
| 2007/0248662 | A1 | 10/2007 | Joshi et al. |
| 2007/0248663 | A1 | 10/2007 | Joshi et al. |
| 2008/0233185 | A1 | 9/2008 | Joshi et al. |
| 2009/0181085 | A1 | 7/2009 | Joshi et al. |
| 2009/0182047 | A1 | 7/2009 | Joshi et al. |
| 2010/0130607 | A1 | 5/2010 | Gold |
| 2010/0316706 | A1 | 12/2010 | Joshi et al. |
| 2011/0112196 | A1 | 5/2011 | Lukashev |
| 2011/0124615 | A1 | 5/2011 | Joshi et al. |

(Continued)

FOREIGN PATENT DOCUMENTS

| CA | 2248955 A1 * | 5/1997 |
|---|---|---|
| CA | 2248955 C | 8/2001 |

(Continued)

OTHER PUBLICATIONS

Andersson, M., et al., "Cytokine profile in interferon-β treated multiple sclerosis patients: reduction of interleukin-10 mRNA expressing cells in peripheral blood," *Eur. J. Neurol.* 4:567-571, Rapid Science Publishers, England (1997).
Becanovic, K., et al., "Paradoxical effects of arthritis-regulating chromosome 4 regions on myelin oligodendrocyte glycoprotein-induced encephalomyelitis in congenic rats," *Eur. J. Immunol.* 33:1907-1916, Wiley-VCH Verlag GmbH & Co., Germany (2003).
Beljaards, R.C. "Ki-I-positive cutaneous lymphoreticular proliferations" *British Journal of Dermatology* 123:533-534, Blackwell Scientific Publications, England (1990).
Correale, J., et al., "Sulfasalazine aggravates experimental autoimmune encephalomyelitis and causes an increase in the number of autoreactive T cells," *J. Neuroimmunol.* 34:109-120, Elsevier Science Publishers B.V., Netherlands (1991).

(Continued)

*Primary Examiner* — Kevin E Weddington
(74) *Attorney, Agent, or Firm* — Sterne, Kessler, Goldstein & Fox P.L.L.C.

(57) ABSTRACT

The present invention relates to the use of certain dialkyl fumarates for the preparation of pharmaceutical preparations for use in transplantation medicine or for the therapy of autoimmune diseases and said compositions in the form of micro-tablets or pellets. For this purpose, the dialkyl fumarates may also be used in combination with conventional preparations used in transplantation medicine and immunosuppressive agents, especially cyclosporines.

5 Claims, No Drawings

(56) References Cited

U.S. PATENT DOCUMENTS

| | | |
|---|---|---|
| 2011/0293711 A1 | 12/2011 | Joshi et al. |
| 2012/0165404 A1 | 6/2012 | Lukashev |
| 2012/0196931 A1 | 8/2012 | Lukashev |

FOREIGN PATENT DOCUMENTS

| | | |
|---|---|---|
| CN | 1125141 A | 6/1996 |
| DE | 25 30 372 A1 | 1/1977 |
| DE | 26 21 214 A1 | 11/1977 |
| DE | 28 40 498 B1 | 8/1979 |
| DE | 35 31 597 A1 | 3/1987 |
| DE | 38 34 794 A1 | 4/1990 |
| DE | 1 972 1099 A1 | 11/1998 |
| EP | 0 188 749 A2 | 7/1986 |
| EP | 0 312 697 A2 | 4/1989 |
| EP | 0 518 388 A2 | 12/1992 |
| EP | 0 793 966 A1 | 9/1997 |
| GB | 1 216 699 | 12/1970 |
| GB | 1 422 726 | 1/1976 |
| GB | 2 291 422 A | 1/1996 |
| JP | 9-221428 A | 8/1997 |
| JP | 10-67783 A | 3/1998 |
| WO | WO 89/01930 A1 | 3/1989 |
| WO | WO 94/28883 A1 | 12/1994 |
| WO | WO 95/25102 A1 | 9/1995 |
| WO | WO 96/01122 A1 | 1/1996 |
| WO | WO 96/02244 A1 | 2/1996 |
| WO | WO 96/27369 A2 | 9/1996 |
| WO | WO 97/09984 A1 | 3/1997 |
| WO | WO 97/39999 A1 | 10/1997 |
| WO | WO 97/44054 A2 | 11/1997 |
| WO | WO 97/48400 A1 | 12/1997 |
| WO | WO 98/04290 A2 | 2/1998 |
| WO | WO 98/27970 A2 | 7/1998 |
| WO | WO 98/30586 A2 | 7/1998 |
| WO | WO 98/52549 A2 | 11/1998 |
| WO | WO 99/21565 A1 | 5/1999 |
| WO | WO 01/59072 A1 | 8/2001 |
| WO | WO 02/02190 A2 | 1/2002 |
| WO | WO 03/032969 A2 | 4/2003 |
| WO | WO 2004/096216 A2 | 11/2004 |
| WO | WO 2005/027899 A1 | 3/2005 |
| WO | WO 2005/044272 A1 | 5/2005 |
| WO | WO 2006/037342 A2 | 4/2006 |
| WO | WO 2006/050730 A1 | 5/2006 |
| WO | WO 2006/055871 A2 | 5/2006 |

OTHER PUBLICATIONS

Dahlman, I., et al., "Quantitative trait loci disposing for both experimental arthritis and encephalomyelitis in the DA rat; impact on severity of myelin oligodendrocyte glycoprotein-induced experimental autoimmune encephalomyelitis and antibody isotype pattern," *Eur. J. Immunol.* 28:2188-2196, Wiley-VCH Verlag GmbH, Germany (1998).

De Graaf, K.L., et al., "MHC Class II Isotype- and Allele-Specific Attenuation of Experimental Autoimmune Encephalomyelitis," *J. Immunol.* 173:2792-2802, American Association of Immunologists, Inc., United States (2004).

De Haan, P., et al., "The Risk of Sensibilization and Contact Urticaria upon Topical Application of Fumaric Acid Derivatives," *Dermatology* 188:126-130, S. Karger AG, Switzerland (1994).

Di Marco, R., et al., "Curative effects of recombinant human Interleukin-6 in DA rats with protracted relapsing experimental allergic encephalomyelitis," *J. Neuroimmunol.* 116:168-177, Elsevier Science Publishers B.V., Netherlands (2001).

Djerbi, M., et al., "Expression of the Long Form of Human FLIP by Retroviral Gene Transfer of Hemopoietic Stem Cells Exacerbates Experimental Autoimmune Encephalomyelitis," *J. Immunol.* 170:2064-2073, American Association of Immunologists, Inc., United States (2003).

Gielen, A.W., et al., "Expression of T cell immunoglobulin- and mucin-domain-containing molecules-1 and -3 (TIM-1 and -3) in the rat nervous and immune systems," *J. Neuroimmunol.* 164:93-104, Elsevier B.V., Netherlands (2005).

Guggenmos, J., et al., "Antibody Cross-Reactivity between Myelin Oligodendrocyte Glycoprotein and the Milk Protein Butyrophilin in Multiple Sclerosis," *J. Immunol.* 172: 661-668, American Association of Immunologists, Inc., United States (2004).

Issazadeh, S., et al., "Cytokine production in the central nervous system of Lewis rats with experimental autoimmune encephalomyelitis: dynamics of mRNA expression for interleukin-10, interleukin-12, cytolysin, tumor necrosis factor α and tumor necrosis factory β," *J. Neuroimmunol.* 61:205-212, Elsevier Science B.V., Netherlands (1995).

Issazadeh, S., et al., "Interferon γ, Interleukin 4 and Transforming Growth Factor β in Experimental Autoimmune Encephalomyelitis in Lewis Rats: Dynamics of Cellular mRNA Expression in the Central Nervous System and Lymphoid Cells," *J. Neurosci. Res.* 40: 579-590, Wiley-Liss, Inc., United States (1995).

Issazadeh, S., et al., "Cytokines in relapsing experimental autoimmune encephalomyelitis in DA rats: persistent mRNA expression of proinflammatory cytokines and absent expression of interleukin-10 and transforming growth factor-β," *J. Neuroimmunol.* 69:103-115, Elsevier Science B.V., Netherlands (1996).

Issazadeh, S., et al., "Major histocompatibility complex-controlled protective influences on experimental autoimmune encephalomyelitis are peptide specific," *Eur. J. Immunol.* 27:1584-1587, VCH Verlagsgesellschaft mbH, Germany (1997).

Khademi, M., et al., "Reduction of both pro- and anti-inflammatory cytokines after 6 months of interferon beta-la treatment of multiple sclerosis," *J. Neuroimmunol.* 103:202-210, Elsevier Science B.V., Netherlands (2000).

Khademi, M., et al., "T Cell Ig- and Mucin-Domain-Containing Molecule-3 (TIM-3) and TIM-1 Molecules Are Differentially Expressed on Human Th1 and Th2 Cells and in Cerebrospinal Fluid-Derived Mononuclear Cells in Multiple Sclerosis," *J. Immunol.* 172: 7169-7176, American Association of Immunologists, Inc., United States (2004).

Khademi, M., et al., "Induction of systemic TNFα in Natalizumab-treated multiple sclerosis," *Eur. J. Neurol.* 15:309-312, EFNS, England (2008).

Kjellén, P., et al., "Genetic influence on disease course and cytokine response in relapsing experimental allergic encephalomyelitis," *Int. Immunol.* 10:333-340, Oxford University Press, England (1998).

Krakauer, M., et al., "Dynamic T-lymphocyte Chemokine Receptor Expression Induced by Interferon-beta Therapy in Multiple Sclerosis," *Scand. J. Immunol.* 64: 155-163, Blackwell Publishing Ltd., England (2006).

Link, H., et al., "Virus-reactive and autoreactive T cells are accumulated in cerebrospinal fluid in multiple sclerosis," *J. Neuroimmunol.* 38:63-74, Elsevier Science Publishers B.V., Netherlands (1992).

Link, J., et al., "Organ-specific Autoantigens Induce Transforming Growth Factor-β mRNA Expression in Mononuclear Cells in Multiple Sclerosis and Myasthenia Gravis," *Annals Neurol.* 35:197-203, American Neurological Association (1994).

Link, J., et al., "Organ-specific autoantigens induce interferon-γ and interleukin-4 mRNA expression in mononuclear cells in multiple sclerosis and myasthenia gravis," *Neurology* 44: 728-734, Lippincott Williams & Wilkins, United States (1994).

Link, J., et al., "Optic neuritis is associated with myelin basic protein and proteolipid protein reactive cells producing interferon-γ, interleukin-4 and transforming growth factor-β," *J. Neuroimmunol,* 49:9-18, Elsevier Science B.V., Netherlands (1994).

Link, J., et al., "Increased Transforming Growth Factor-β, Interleukin-4, and Interferon-γ in Multiple Sclerosis," *Ann. Neurol.* 36:379-386, American Neurological Association, United States (1994).

Lobell, A., et al., "Vaccination with DNA Encoding an Immunodominant Myelin Basic Protein Peptide Targeted to Fc of Immunoglobulin G Suppresses Experimental Autoimmune Encephalomyelitis," *J. Exp. Med.* 187:1543-1548, Rockefeller University Press, United States (1998).

Lobell, A., et al., "Presence of CpG DNA and the Local Cytokine Milieu Determine the Efficacy of Suppressive DNA Vaccination in Experimental Autoimmune Encephalomyelitis," *J. Immunol.* 163:4754-4762, American Association of Immunologists, United States (1999).

Lobell, A., et al., "Suppressive DNA Vaccination in Myelin Oligodendrocyte Glycoprotein Peptide-Induced Experimental Autoimmune Encephalomyelitis Involves a T1-Biased Immune Response," *J. Immunol.* 170:1806-1813, American Association of Immunologists, Inc., United States (2003).

Lorentzen, J.C., et al., "Protracted, relapsing and demyelinating experimental autoimmune encephalomyelitis in DA rats immunized with syngeneic spinal cord and incomplete Freund's adjuvant," *J. Neuroimmunol.* 63:193-205, Elsevier Science B.V., Netherlands (1995).

Lorentzen, J.C., et al., "Genetic analysis of inflammation, cytokine mRNA expression and disease course of relapsing experimental autoimmune encephalomyelitis in DA rats," *J. Neuroimmunol.* 80:31-37, Elsevier Science B.V., Netherlands (1997).

Matusevicius, D., et al., "Autoantigen-induced IL-13 mRNA expression is increased in blood mononuclear cells in myasthenia gravis and multiple sclerosis," *Eur. J. Neurol.* 4:468-475, Rapid Science Publishers, England (1997).

Muhallab, S., et al., "Intra-CNS activation by antigen-specific T lymphocytes in experimental autoimmune encephalomyelitis," *J. Neuroimmunol.* 113:202-211, Elsevier Science B.V., Netherlands (2001).

Mustafa, M.I., et al., "T cell immunity and interferon-γ secretion during experimental allergic encephalomyelitis in Lewis rats," *J. Neuroimmunol.* 31:165-177, Elsevier Science B.V., Netherlands (1991).

Mustafa, M., et al., "Immunopharmacologic Modulation of Experimental Allergic Encephomyelitis: Low-Dose Cyclosporin-A Treatment Causes Disease Relapse and Increased Systemic T and B Cell-Mediated Myelin-Directed Autoimmunity," *Scand. J. Immunol.* 38:499-507, Blackwell Publishing Ltd., England (1993).

Mustafa, M., et al., "The major histocompatibility complex influences myelin basic protein 63-88-induced T cell cytokine profile and experimental autoimmune encephalomyelitis," *Eur. J. Immunol.* 23:3089-3095, VCH Verlagsgesellschaft mbH, Germany (1993).

Mustafa, M., et al., "Protective Influences on Experimental Autoimmune Encephalomyelitis by MHC Class I and Class II Alleles," *J. Immunol.* 153:3337-3344, American Association of Immunologists, United States (1994).

Navikas, V., et al., "Increased mRNA Expression of IL-10 in Mononuclear Cells in Multiple Sclerosis and Optic Neuritis," *Scand. J. Immunol.* 41:171-178, Blackwell Publishing Ltd., England (1995).

Navikas, V., et al., "Augmented expression of tumour necrosis factor-α and lymphotoxin in mononuclear cells in multiple sclerosis and optic neuritis," *Brain* 119:213-223, Oxford University Press, England (1996).

Nieboer, C., et al., "Fumaric Acid Therapy in Psoriasis: A Double Blind Comparison between Fumaric Acid Compound Therapy and Monotherapy with Dimethylfumaric Acid Ester," *Dermatologica* 181:33-37, Karger AG, Switzerland (1990).

Nieboer, C., et al., "Treatment of psoriasis with fumaric acid derivatives," in the Proceedings of the 239th N.S.D.V. Meeting, *Br. J. Dermatol.* 117(6):791-792, Blackwell Scientific Publications, England (1987).

Olsson, T., et al., "Autoreactive T Lymphocytes in Multiple Sclerosis Determined by Antigen-induced Secretion of Interferon-γ," *J. Clin. Invest.* 86: 981-985, American Society for Clinical Investigation, United States (1990).

Olsson, T., et al., "Increased numbers of T cells recognizing multiple myelin basic protein epitopes in multiple sclerosis," *Eur. J. Immunol.* 22:1083-1087, VCH Verlagsgesellschaft mbH, Germany (1992).

Olsson, T., "Cytokines in neuroinflammatory disease: role of myelin autoreactive T cell production of interferon-gamma," *J. Neuroimmunol.* 40:211-218, Elsevier Science Publishers B.V., Netherlands (1992).

Olsson, T., "Cerebrospinal Fluid," *Ann. Neurol.* 36:S100-S102, American Neurological Association, United States (1994).

Olsson, T., "Role of cytokines in multiple sclerosis and experimental autoimmune encephalomyelitis," *Eur. J. Neurol.* 1:7-19, Rapid Communications of Oxford Ltd., England (1994).

Olsson, T., "Critical Influences of the Cytokine Orchestration on the Outcome of Myelin Antigen Specific T-Cell Autoimmunity in Experimental Autoimmune Encephalomyelitis and Multiple Sclerosis," *Immunological Reviews* 144:245-268, Munksgaard, Denmark (1995).

Olsson, T., "Chapter 6: Cytokines in Multiple Sclerosis and Its Experimental Models," *Neuroscience Intelligence Unit 5: T-Cell Autoimmunity and Multiple Sclerosis* pp. 91-112, R.G. Landes Company, United States (1999).

Olsson, T., "Future prospects of cytokines in the pathogenesis and management of multiple sclerosis," *Frontiers in Multiple Sclerosis* 2:139-150, Martin Dunitz Publishers Ltd., United Kingdom (1999).

Olsson, T., et al., "MHC and Non-MHC Genetics of Experimental Autoimmune Encephalomyelitis," *From Basic Immunology to Immune-Mediated Demyelination*, pp. 246-264, Springer-Verlag, Italy (1999).

Olsson, T., et al., "Genetics of rat neuroinflammation," *J. Neuroimmunol.* 107:191-200, Elsevier, Netherlands (2000).

Olsson, T., et al., "Depletion of Vβ5.2/5.3 T cells with a humanized antibody in patients with multiple sclerosis," *Eur. J. Neurol.* 9:153-164, EFNS, England (2002).

Olsson, T., et al., "Harm or heal—divergent effects of autoimmune neuroinflammation?," *Trends Immunol.* 24(1):5-6, Elsevier Science Ltd., England (2003).

Robinson, W.H., et al., "Protein microarrays guide tolerizing DNA vaccine treatment of autoimmune encephalomyelitis," *Nat. Biotechnol.* 21(9):1033-1039, Nature Publishing Group, England (2003).

Ros, J.J.W., et al., "Therapie bij psoriasis" *Pharmaceutisch Weekblad* 126(13):309-319, D B Centens Witgeversmij, Netherlands (1991).

Ruuls, S.R., et al., "The Length of Treatment Determines Whether IFN-β Prevents or Aggravates Experimental Autoimmune Encephalomyelitis in Lewis Rats," *J. Immunol.* 157:5721-5731, American Association of Immunologists, United States (1996).

Söderström, M., et al., "T Cells Recognizing Multiple Peptides of Myelin Basic Protein are Found in Blood and Enriched in Cerebrospinal fluid in Optic Neuritis and Multiple Sclerosis," *Scand. J. Immunol.* 37:355-368, Blackwell Scientific Publications, England (1993).

Sun, J.B., et al., "Treatment of experimental autoimmune encephalomyelitis by feeding myelin basic protein conjugated to cholera toxin B subunit," *Proc. Natl. Acad Sci. USA* 93:7196-7201, National Academy of Sciences, United States (1996).

Van Loenen, A.C., et al., "Fumaarzuurtherapie: van fictie tot werkelijkheid?" *Pharmaceutisch Weekblad* 124(45):894-900, D B Centens Witgeversmij, Netherlands (1989).

Wallström, E., et al., "Memantine abrogates neurological deficits, but not CNS inflammation, in Lewis rat experimental autoimmune encephalomyelitis," *J. Neurol. Sci.* 137(2):89-96, Elsevier Science B.V., Netherlands (1996).

Wallström, E., et al., "Increased reactivity to myelin oligodendrocyte glycoprotein peptides and epitope mapping in HLA DR2(15)+ multiple sclerosis," *Eur. J. Immunol.* 28:3329-3335, Wiley-VCH Verlag GmbH, Germany (1998).

Wang, W.Z., et al., "Myelin antigen reactive T cells in cerebrovascular diseases," *Clin. Exp. Immunol.* 88:157-162, Blackwell Scientific Publications, England (1992).

Weissert, R., et al., "Protective DNA vaccination against organ-specific autoimmunity is highly specific and discriminates between single amino acid substitutions in the peptide autoantigen," *PNAS* 97(4):1689-1694, National Academy of Sciences, United States (2000).

Balashov, K.E., et al., "Defective regulation of IFNγ and IL-12 by endogenous IL-10 in progressive MS," *Neurology* 55(2):192-198, AAN Enterprises, Inc., United States (2000).

Bettelli, E. and Nicholson, L.B., "The Role of Cytokines in Experimental Autoimmune Encephalomyelitis," *Arch. Immunol. Ther. Exp.* 48:389-398, Birkhauser, Switzerland (2000).

Brown, T.R. and Kraft, G.H., "Multiple Sclerosis: A Paradigm Shift," *Phys. Med. Rehabil. Clin. N. Am.* 16:xvii-xx, Elsevier Inc., England (2005).

Cannella, B., et al., "IL-10 Fails to Abrogate Experimental Autoimmune Encephalomyelitis," *J. Neurosci. Res.* 45:735-746, Wiley-Liss, Inc., United States (1996).

Dal Canto, R.A., et al., "Local Delivery of TNF by Retrovirus-Transduced T Lymphocytes Exacerbates Experimental Autoimmune Encephalomyelitis," *Clin. Immunol.* 90(1):10-14, Academic Press, United States (1999).

Robinson, J.R. of Darby & Darby, Letter to Susan H. Alexander, Esq., General Counsel, Biogen Idec., dated Dec. 11, 2007, 2 pages.

Del Prete, G., "The Concept of Type-1 and Type-2 Helper T Cells and Their Cytokines in Humans," *Int. Rev. Immunol.* 16:427-455, OPA, Netherlands (1998).

Di Rosa, F., et al., "Lack of Th2 cytokine increase during spontaneous remission of experimental allergic encephalomyelitis," *Eur. J. Immunol.* 28(12):3893-3903, Wiley-VCH Verlag GmbH, Germany (1998).

Ferber, I.A., et al., "Mice with a Disrupted IFN-γ Gene Are Susceptible to the Induction of Experimental Autoimmune Encephalomyelitis (EAE)," *J. Immunol.* 156(1):5-7, American Association of Immunologists, United States (1996).

Ferrante, P., et al., "Cytokine Production and Surface Marker Expression in Acute and Stable Multiple Sclerosis: Altered IL-12 Production and Augmented Signaling Lymphocytic Activation Molecule (SLAM)—Expressing Lymphocytes in Acute Multiple Sclerosis," *J. Immunol.* 160(3):1514-1521, American Association of Immunologists, United States (1998).

Furlan, R., et al., "Interferon-β treatment in multiple sclerosis patients decreases the number of circulating T cells producing interferon-γ and interleukin-4," *J. Neuroimmunol.* 111:86-92, Elsevier Science B.V., Netherlands (2000).

Galli, G., et al., "Macrophage-derived chemokine production by activated human T cells in vitro and in vivo: preferential association with the production of type 2 cytokines," *Eur. J. Immunol.* 30:204-210, Wiley-VCH Verlag GmbH, Germany (2000).

Genain, C.P., et al., "Late Complications of Immune Deviation Therapy in a Nonhuman Primate," *Science* 274(5292):2054-2057, American Association for the Advancement of Science, United States (1996).

Gijbels, K., et al., "Administration of Neutralizing Antibodies to Interleukin-6 (IL-6) Reduces Experimental Autoimmune Encephalomyelitis and Is Associated with Elevated Levels of IL-6 Bioactivity in Central Nervous System and Circulation," *Mol. Med.* 1(7): 795-805, Blackwell Scientific Publications, United States (1995).

Giovannoni, G. and Miller, D.H., "Multiple sclerosis and its treatment," *J. R. Coll. Physicians Lond.* 33(4):315-322, Royal College of Physicians of London, England (1999).

Hemmer, B., et al., "Cytokine Phenotype of Human Autoreactive T Cell Clones Specific for the Immunodominant Myelin Basic Protein Peptide (83-99)," *J. Neurosci. Res.* 45:852-862, Wiley-Liss Inc., United States (1996).

Hintzen, R.Q. and Polman, C.H., "Th-cell modulation in multiple sclerosis," *Immunol. Today* 18(10):507-508, Elsevier Science Publishers, England (1997).

Hultgren, B., et al., "Genetic Absence of γ-Interferon Delays but Does Not Prevent Diabetes in NOD Mice," *Diabetes* 45:812-817, American Diabetes Association, United States (1996).

Krakowski, M., and Owens, T., "Interferon-γ confers resistance to experimental allergic encephalomyelitis," *Eur. J. Immunol.* 26:1641-1646, VCH Verlagsgesellschaft mbH, Germany (1996).

Lafaille, J.J., et al., "Myelin Basic Protein-specific T Helper 2 (Th2) Cells Cause Experimental Autoimmune Encephalomyelitis in Immunodeficient Hosts Rather than Protect Them from the Disease," *J. Exp. Med.* 186(2):307-312, Rockefeller University Press, United States (1997).

Lafaille, J.J., "The Role of Helper T Cell Subsets in Autoimmune Diseases," *Cytokine & Growth Factor Reviews* 9(2):139-151, Elsevier Science Ltd., England (1998).

Laman, J.D., et al., "Balancing the Th1/Th2 concept in multiple sclerosis," *Immunol. Today* 19(11):489-490, Elsevier Science Publishers, England (1998).

The Lenercept Multiple Sclerosis Study Group and the University of British Columbia MS/MRI Analysis Group, "TNF neutralization in MS: Results of a randomized, placebo-controlled multicenter study," *Neurology* 53:457-465, AAN Enterprises, United States (1999).

Liedtke, W., et al., "Effective Treatment of Models of Multiple Sclerosis by Matrix Metalloproteinase Inhibitors," *Ann. Neurol.* 44:35-46, American Neurological Association, United States (1998).

Link, H., "The cytokine storm in multiple sclerosis," *Mult. Scler.* 4:12-15, SAGE Publications, England (1998).

Lopez, E., et al., "Interferon γ, IL2, IL4, IL10 and TNFα Secretions in Multiple Sclerosis Patients Treated with an Anti-CD4 Monoclonal Antibody," *Autoimmunity* 29:87-92, OPA, Netherlands (1999).

Lyons, J.-A. et al., "Pathogenesis of acute passive murine encephalomyelitis II. Th1 phenotype of the inducing population is not sufficient to cause disease," *J. Neuroimmunol.* 93:26-36, Elsevier Science B.V., Netherlands (1999).

Määttä, J.A., et al., "Neutrophils secreting tumor necrosis factor alpha infiltrate the central nervous system of BALB/c mice with experimental autoimmune encephalomyelitis," *J. Neuroimmunol.* 90:162-175, Elsevier Science B.V., Netherlands (1998).

Martin, R., et al., "T helper cell differentiation in multiple sclerosis and autoimmunity," *Immunol. Today* 19(11):495-498, Elsevier Science Publishers, England (1998).

Mattner, F., et al., "Inhibition of Tn1 development and treatment of chronic-relapsing experimental allergic encephalomyelitis by a non-hypercalcemic analogue of 1,25-dihydroxyvitamin $D_3$," *Eur. J. Immunol.* 30:498-508, Wiley-VCH Verlag GmbH, Germany (2000).

O'Garra, A., et al., "$CD4^+$ T-cell subsets in autoimmunity," *Curr. Opin. Immunol.* 9:872-883, Current Biology Ltd., United States (1997).

Olsson, T., "Cytokine-producing cells in experimental autoimmune encephalomyelitis and multiple sclerosis," *Neurology* 45(Suppl 6): S 11-S15, Lippincott Williams & Wilkins, United States (1995).

Panitch, H.S. et al., "Exacerbations of Multiple Sclerosis in Patients Treated with Gamma Interferon," *The Lancet* 1:893-895, Lancet Publishing Group, England (1987).

Perrella, O., et al., "Interleukin-10 and IFN-α in multiple sclerosis: is there a balance?," *J. Neurovirol.* 3(Suppl.):P17, Stockton Press, United States (1997).

Pette, M., et al., "Differential effects of phosphodiesterase type 4-specific inhibition on human autoreactive myelin-specific T cell clones," *J. Neuroimmunol.* 98:147-156, Elsevier Science B.V., Netherlands (1999).

Ristori, G., et al., "T cell response to myelin basic protein before and after treatment with interferon beta in multiple sclerosis," *J. Neuroimmunol.* 99:91-96, Elsevier Science B.V., Netherlands (1999).

Rohowsky-Kochan, C., et al., "Impaired interleukin-12 production in multiple sclerosis patients," *Mult. Scler.* 5:327-334, SAGE Publications, England (1999).

Rohowsky-Kochan, C., et al., Cytokine secretion profile of myelin basic protein-specific T cells in multiple sclerosis, *Mult. Scler.* 6:69-77, SAGE Publications, England (2000).

Romagnani, S., "The Th1/Th2 paradigm," *Immunol. Today* 18(6):263-266, Elsevier Science Ltd., England (1997).

Rook, G.A.W., et al., "Bacterial vaccines for the treatment of multiple sclerosis and other autoimmune diseases," *Immunol. Today* 21(1):503-508, Elsevier Science Ltd., England (2000).

Samoilova, E.B., et al., "Experimental Autoimmune Encephalomyelitis in Intercellular Adhesion Molecule-1-Deficient Mice," *Cell. Immunol.* 190:83-89, Academic Press, United States (1998).

Singh, V.K., et al., "The Paradigm of Th1 and Th2 Cytokines. Its Relevance to Autoimmunity and Allergy," *Immunol. Res.* 20:147-161, Humana Press Inc., United States (1999).

Sinigaglia, F., et al., "Type I interferons and the Th1/Th2 paradigm," *Dev. Comp. Immunol.* 23:657-663, Elsevier Science Ltd., United States (1999).

Smeltz, R.B. and Swanborg, R.H., "Concordance and Contradiction Concerning Cytokines and Chemokines in Experimental Demyelinating Disease," *J. Neurosci. Res.* 51:147-153, Wiley-Liss, Inc., United States (1998).

Zhu, J., et al., "Cytokine production and the pathogenesis of experimental autoimmune neuritis and Guillain-Barré syndrome," *J. Neuroimmunol*, 84:40-52, Elsevier Science B.V., Netherlands (1998).

Zipp, F., "No Evidence for Generation of Th-2-like MBP-Specific T-Cell Lines by Blockade of the Costimulatory Molecule B7-1," *Scand J. Immunol.* 52:510-514, Blackwell Science Ltd., England (2000).

Andersen, K.E., et al., "Contact dermatitis: A Review," *Contact Dermatitis* 16:55-78, Munksgaard, Denmark (1987).

De Jong, R., et al., "Selective stimulation of T helper 2 cytokine responses by the anti-psoriasis agent monomethylfumarate," *Eur. J. Immunol.* 26:2067-2074, Verlag Chemie GmbH, Germany (1996).

Dücker, P. and Pfeiff, B., "Zwei Fälle von Nebenwirkungen einer Fumarsäureester—Lokaltharapie," *H+G Zeitschrift für Hautkrankheiten* 65:734-736, Grosse Verlag Berlin, Germany (1990) (Abstract Only in English).

Fliegner, L. and Spiegel, P., "Osteomalazie als offenbar seltene Nebenwirkung der oralen Fumarsäuretherapie," *Hautarzt* 43:554-560, Springer-Verlag, Germany (1992) (Abstract Only in English).

Ghoreschi, K., et al., "Fumarates induce a DC2 phenotype in dendritic cells that establishes protective Th2 responses," *Arch. Dermatol. Forschung* 296:420, Springer Verlag, Germany (2005) (Abstract Only).

Ghoreschi, K., et al., "Fumaric acid ester an antipsoriatic drug abolishes the capacity of T cells to induce Th1-mediated autoimmune disease," *Arch. Dermatol. Res.* 294:28, Springer Verlag, Germany (2002) (Abstract Only).

Ghoreschi, K. and Röcken, M., "Immune Deviation Strategies in the Therapy of Psoriasis," *Current Drug Targets—Inflammation & Allergy* 3:193-198, Bentham Science Publishers Ltd., Netherlands (2004).

Hunziker, T. and Schmidli, J., "Psoriasis, eine Autoimmunkrankheit?" *Therapeutische Umschau* 50:110-113, Determatologische Klinik der Universität Bern, Switzerland (1993).

International Search Report for International Application No. PCT/EP99/08215, European Patent Office, Rijswijk, Netherlands, mailed on Jul. 12, 2000.

Kiehl, R. and Ionescu, G., "A Defective Purine Nucleotide Synthesis Pathway in Psoriatic Patients," *Acta Derm. Venereol. (Stockh)* 72:253-255, Society for the Publication of Acta Dermato-Venerologica, Sweden (1992).

Kolbach, D.N. and Nieboer, C., "Fumaric acid therapy in psoriasis: Results and side effects of 2 years of treatment," *J. Am. Acad. Derm.* 27(5):769-771, Mosby, United States (1992).

Lahti, A. and Maibach, H.I., "Contact urticaria from diethyl fumarate," *Contact Dermatitis* 12:139-140, Munksgaard, Denmark (1985).

*The Merck Index: An Encyclopedia of Chemicals, Drugs, and Biologicals*, 10$^{th}$ Edition, p. 396, Windholz, M., et al., eds., Merck & Co., Inc., United States (1983).

Nieboer, C., et al., "Systemic therapy with fumaric acid derivates: New possibilities in the treatment of psoriasis," *J. Am. Acad. Dermatol.* 20:601-608, Mosby, United States (1989).

Peeters, A.J., et al., "Gunstig effect van fumaarzuurtherapie bij arthritis psoriatica: een dubbelblind, placebo-gecontroleerd onderzoek," *Ned. Tijdschr. Geneeskd.* 136(49):2428-2431, Bohn Stafleu van Loghum, Netherlands (1992) (Abstract Only in English).

Sadjak, A. et al., "Nephrotoxische Wirkung von Fumarsaurederivaten," *Deutsch Med. Wochenschr.* 116:478, G. Thieme, Germany (1991).

Schilling, S., et al., "Fumaric acid esters are effective in chronic experimental autoimmune encephalomyelitis and suppress macrophage infiltration," *Clin. Exp. Immunol.* 145:101-107, British Society for Immunology, England (2006).

Schilling, F. and Schopf, R.E., "Adultes Debré-de Toni-Fanconi-Syndrom mit Osteomalazie, erworben durch Langzeittherapie einer Psoriasis mit Fumarsäureester—zugleich ein Beitag zur malazischen Osteoarthropathie," *Akt. Rheumatol.* 24(6):174-179, Georg Thieme Verlag, Germany (1999) (Abstract Only in English).

Schimrigk, S., et al., "Oral fumaric acid esters for the treatment of active multiple sclerosis: an open-label, baseline-controlled pilot study," *Eur. J. Neurol.* 13:604-610, EFNS, England (2006).

Sebok, B., et al., "Effect of Fumaric Acid, Its Dimethylester, and Topical Antipsoriatic Drugs on Epidermal Differentiation in the Mouse Tail Model," *Skin Pharm.* 9:99-103, S. Karger AG, Switzerland (1996).

Thio, H.B., et al., "Fumaric acid derivatives evoke a transient increase in intracellular free calcium concentration and inhibit the proliferation of human keratinocytes," *Brit. J. Dermatol.* 131:856-861, Blackwell Scientific Publications, England (1994).

Dialog File 351, Accession No. 8397165, Derwent WPI English language abstract for CN 1125141 A (1996) (listed as document FP2 on accompanying form PTO/SB/08A).

Dialog File 351, Accession No. 3972689, Derwent WPI English language abstract for DE 35 31 597 Al (1987) (listed as document FP5 on accompanying form PTO/SB/08A).

Altmeyer, P. and Nüchel, C., "Systemtherapie der Psoriasis," *Dtsch. med. Wschr.* 121:1605-1607, Georg Thieme Verlag, Germany (1996).

Bacharach-Buhles, M., et al.,"Fumaric Acid Esters (FAEs) Suppress CD 15- and ODP 4-positive Cells in Psoriasis," *Acta. Derm. Venereal. Suppl(Stockh)* 186:79-82, Scandinavian University Press, Norway (1994).

Ockenfels, H.M., et al., "The antipsoriatic agent dimethylfumarate inununomodulates T-cell cytokine secretion and inhibits cytokines of the psoriatic cytokine network," *Br. J. Dermatol.* 139:390-395, British Association of Dermatologists, England (1998).

Gasser, M., et al., "Host Vs Graft and Graft Vs Host Reactions After Allogeneic Heterotopic Small Bowel Transplantation in the Rat," *Transplant. Proc.* 24(3):1128-1129, Appleton & Lange, United States (1992).

Nathens, A.B., et al., "The Glutathione Depleting Agent Diethylmaleate Prolongs Renal Allograft Survival," *Journal of Surgical Research* 77:75-79, Academic Press, United States (1998).

Nibbering, P.H., et al., "Intracellular signalling by binding sites for the antipsoriatic agent monomethylfumarate on human granulocytes," *Br. J. Dermatol.* 137:65-75, British Association of Dermatologists, England (1997).

Nibbering, P.H., et al., "Effects of Monomethylfumarate on Human Granulocytes," *J. Invest. Dermatol.* 101:37-42, The Society for Investigative Dermatology, Inc., United States (1993).

Sebök, B., et al., "Antiproliferative and cytotoxic profiles of antipsoriatic fumaric acid derivatives in keratinocyte cultures," *Eur. J. Pharmacol.* 270:79-87, Elsevier Science B.V., Netherlands (1994).

Schwinghammer, T.L. and Bloom, E.J., "Pharmacologic prophylaxis of acute graft-versus-host disease after allogeneic marrow transplantation," *Clinical Pharm.* 12:736-761, American Society of Hospital Pharmacists, Inc., United States (1993).

Bayard, W., et al., "Perorale Langzeitbehandlung der Psoriasis mit Fumarsäurederivaten" *Hautarzt* 38:279-285, Springer-Verlag, Germany (1987) (Abstract Only in English).

*The Merck Manual of Diagnosis and Therapy*, 15$^{th}$ Edition, Berkow, R. and Fletcher, A.J., eds., p. 327, Merck Sharp & Dohme Research Lab, United States (1987).

*Immunmodulation durch Fumaderm. Das richtungsweisende Konzept*, Charite-Berlin Hautklinik Symposium, Nov. 1-3, 1996, p. 1-27.

Partial English language translation, 4 pages, of *Immunmodulation durch Fumaderm. Das richtungsweisende Konzept*, Charite-Berlin Hautklinik Symposium, Nov. 1-3, 1996, p. 1-27.

Amamoto, T., et al., "Effect of E-64, Thiol Protease Inhibitor, on the Secondary Anti-SRBC Response In Vitro," *Microbiol. Immunol.* 28(1):85-97, Center for Academic Publications, Australia (1984).

Barrett, A.J. et al., "L-*trans*-Epoxysuccinyl-leucylamido(4-guanidino)butane (E-64) and its analogues as inhibitors of cysteine proteinases including cathepsins B, H and L," *Biochem. J.* 201:189-198, The Biochemical Society, England (1982).

Bellier, B., et al., "Replacement of Glycine with Dicarbonyl and Related Moieties in Analogues of the C-Terminal Pentapeptide of Cholecystokinin: $CCK_2$ Agonists Displaying a Novel Binding Mode," *J. Med. Chem.* 43:3614-3623, American Chemical Society, United States (2000).

Birch, A.J., et al., "Metabolites of *Aspergillus indicus*: The Structure and Some Aspects of the Biosynthesis of Dihydrocanadensolide," *Aust. J. Chem.* 21:2775-2784, CSIRO Publishing, Australia (1968).

Choo, H.-Y.P., et al., "Design and synthesis of α,β-unsaturated carbonyl compounds as potential ACE inhibitors," *Eur. J. Med. Chem.* 35:643-648, Éditions scientifiques et médicales Elsevier SAS, France (2000).

Dethlefsen, L.A., et al. "Toxic Effects of Acute Glutathione Depletion by Buthionine Sulfoximine and Dimethylfumarate on Murine Mammary Carcinoma Cells," *Radiation Res.* 114:215-224, Academic Press, Inc., United States (1988).

Galpin, I.J., et al., "The Synthesis of an Insulin Active Site Analogue," *Tetrahedron* 39(1):149-158, Pergamon Press Ltd., England (1983).

Gerhard, U., et al., "The Free Energy Change of Restricting a Bond Rotation in the Binding of Peptide Analogues to Vancomycin Group Antibiotics," *Bioorganic & Medicinal Chemistry Letters* 3(5):803-808, Pergamon Press Ltd., England (1993).

Gordon, G.B., et al., "Induction of NAD(P)H:quinone reductase in human peripheral blood lymphocytes, " *Carcinogenesis* 12(12):2393-2396, Oxford University Press, England (1991).

Griehl, C. and Jeschkeit, H., "α-Aspartyl Peptides by Addition of Amines to N-Maleylamino Acid Derivatives," *Chemistry of Peptides and Proteins* 5/6(Pt. A):99-103, Germany (1993).

Hildebrandt, H., "Pschyrembel Klinisches Wörterbuch 258," *Auflage*, p. 182 and p. 1469, Walter de Gruyter, Berlin, Germany (1998).

Hohenegger, M., et al., "Nephrotoxicity of Fumaric Acid Monoethylester (FAME)," *Advances in Experimental Medicine and Biology* 252:265-272, Kluwer Academic, United States (1989).

Holroyd, S,E., et al., "Rational Design and Binding of Modified Cell-Wall Peptides to Vancomycin-Group Antibiotics: Factorising Free Energy Contributions to Binding," *Tetrahedron* 49(41):9171-9182, Pergamon Press Ltd, England (1993).

Kamiyama, T., et al., "Ro 09-1679, A Novel Thrombin Inhibitor," *The Journal of Antibiotics* 45(3):424-427, Japan Antibiotics Research Association, Japan (Mar. 1992).

Krstenansky, J.L., et al., "Development of MDL 28,050, a Small Stable Antithrombin Agent Based on a Functional Domain of the Leech Protein, Hirudin," *Thrombosis and Haemostasis* 63(2):208-214, F.K. Schattauer Verlagsgesellschaft mbH (Stuttgart), Germany (1990).

Kuroda, K., et al., "Fumaric Acid Enhances DNA Synthesis of Rat Hepatocytes by Counteracting the Toxicities of Mitomycin C and Aflatoxin $B_1$," *Jpn. J. Cancer Res. (Gann)* 77:750-758, Japanese Cancer Association, Japan (1986).

Biosis Database, Accession No. PREV197662032843, English language abstract for Kuroda, K., et al., "Inhibitory Effect of Capsella-Bursa-Pastoris Extract on Growth of Ehrlich Solid Tumor in Mice," *Cancer Res.* 36(6):1900-1903, American Association for Cancer Research, United States (1976) (Abstract Only).

Langlois, M., et al., "Synthesis of symmetrical pseudopeptides as potential inhibitors of the human immunodeficiency virus-1 protease," *Eur. J. Med. Chem.* 29:639-647, Elsevier, Paris, France (1994).

Lehnert, S., et al., "Radiation Response of Drug-Resistant Variants of a Human Breast Cancer Cell Line: The Effect of Glutathione Depletion," *Radiation Res.* 124:208-215, Academic Press, Inc., United States (1990).

Miller, A.C., et al., "Posttranscriptional Down-Regulation of *ras* Oncogene Expression by Inhibitors of Cellular Glutathione," *Molecular and Cellular Biology* 13:4416-4422, American Society for Microbiology, United States (1993).

Mrowietz, U., "Nephrotoxische Wirkung durch Fumarsäure," *Hautarzt* 51:615, Springer-Verlag, Germany (2000).

Odom, R.Y., et al., "Cancer Chemoprotective Agents Inhibition of Human HT29 Colon Carcinoma Cell Proliferation is Reversed by N-Acetyl Cysteine," *Proc. Amer. Assoc. for Cancer Res. Annual* 41:342, Cancer Research, Inc., United States (2000).

Ondrus, V., et al., "A Simple Synthesis of Some Analogues of Natural Antibiotics," *Chem. Papers* 51:164-166, Versita, England (1997).

Orta, T., et al., "Glutathione manipulation and the radiosensitivity of human tumour and fibroblast cell lines," *Int. J. Radiat. Biol.* 68:413-419, Taylor & Francis Ltd., England (1995).

Biosis Database, Accession No. PREV199497368291, English language abstract for Pearl, J.M., et al., "Fumarate-enriched blood cardioplegia results in complete functional recovery of immature myocardium," *Ann. Thorac. Surg.* 57(6):1636-1641, Elsevier, Netherlands (1994) (Abstract Only).

Peeters, A.J., et al., "Fumaric Acid Therapy for Psoriatic Arthritis. A Randomized, Double-blind, Placebo-controlled Study," *Br. J. Rheumatol.* XXXI(7):502-504, British Association for Rheumatology and Rehabilitation, England (1992).

Pereira, M.A., et al., "Use of azoxymethane-induced foci of aberrant crypts in rat colon to identify potential cancer chemopreventive agents," *Carcinogenesis* 15(5):1049-1054, Oxford University Press, England (1994).

Portoghese, P.S., et al., "Synthesis and Biological Activity of Analogues of β- Chlornaltrexamine and β-Funaltrexamine at Opioid Receptors," *J. Med. Chem.* 29:1861-1864, American Chemical Society, United States (1986).

Prochaska, H.J., et al., "Elevation of Glutathione Levels by Phase II Enzyme Inducers: Lack of Inhibition of Human Immunodeficiency Virus Type 1 Replication in Chronically Infected Monocytoid Cells," *Mol. Pharmacol.* 45:916-921, The American Society for Pharmacology and Experimental Therapeutics, United States (1994).

Prochaska, H.J., et al., "Oltipraz, an inhibitor of human immunodeficiency virus type 1 replication," *Proc. Natl. Acad. Sci. USA* 90:3953-3957, National Academy of Sciences, United States (1993).

Rao, C.V., et al., "Chemoprevention of Azoxymethane-Induced Colon Cancer by Ascorbylpalmitate, Carbenoxolone, Dimethylfumarate and *p*-Methoxyphenol in Male F344 Rats," *Anticancer Res.* 15:1199-1204, Anticancer Research, Greece (1995).

Rao, K.S. and Mishra, S.H., "Antihepatotoxic activity of monomethyl fumarate isolated from *Fumaria indica*," *J. Ethnopharmacol.* 60:207-213, Elsevier Science Ireland Ltd., Ireland (1998).

Roodnat, J.I., et al., "Akute Niereninsuffizienz bei der Behandlung der Psoriasis mit Fumasäure-Estern," *Schweiz. med. Wschr.* 119:826-830, Basel, B. Schwabe & Co., Switzerland (1989) (Abstract Only in English).

Rossi, D., et al., "Approach to the Use of Benzylpenicillinacylase for Configurational Correlations of Amino Compounds. 2. Hydrolysis of N-(p-Aminophenylacetyl) Derivatives of Some Chiral Primary Amines," *J. Org. Chem.* 44:2222-2225, American Chemical Society, United States (1979).

Schirmeister, T., "Aziridine-2,3-dicarboxylic Acid Derivatives as Inhibitors of Papain," *Arch. Pharm. Pharm. Med. Chem.* 329:239-244, VCH Verlagsgesellschaft mbH, Germany (1996).

Biosis Database, Accession No. PREV199699044855, English language abstract for Schmidt, K.N, et al., "Anti-psoriatic drug anthralin activates transcription factor NF-kappa-B in murine keratinocytes," *J. Immunol.* 156(11):4514-4519, American Association of Immunologists, United States (1996) (Abstract Only).

Spencer, S.R, et al., "Induction of Glutathione Transferases and NAD(P)H:Quinone Reductase by Fumaric Acid Derivatives in Rodent Cells and Tissues," *Cancer Res.* 50:7871-7875, American Association for Cancer Research, United States (1990).

Steele, V.E., et al., "Preclinical Efficacy Evaluation of Potential Chemopreventive Agents in Animal Carcinogenesis Models: Methods and Results From the NCI Chemoprevention Drug Development Program," *J. Cellular Biochemistry* S20:32-54, Wiley-Liss, Inc., United States (1994).

Su, J.Y.C., et al., "Reduction of $H_2O_2$-evoked, intracellular calcium increases in the rat N18-RE-105 neuronal cell line by pretreatment with an electrophilic antioxidant inducer," *Neurosci. Lett.* 273:109-112, Elsevier Science Ireland Ltd., Ireland (1999).

Subasinghe, N., et al., "Synthesis of Acyclic and Dehydroaspartic Acid Analogues of Ac-Asp-Glu-OH and Their Inhibition of Rat Brain N-Acetylated α-Linked Acidic Dipeptidase (NAALA Dipeptidase)," *J. Med. Chem.* 33:2734-2744, American Chemical Society, United States (1990).

Vandermeeren, M., et al., "Dimethylfumarate is an Inhibitor of Cytokine-Induced Nuclear Translocation of NF-kB1, But Not RelA in Normal Human Dermal Fibroblast Cells," *J. Inves. Dermatol.* 116:124-130, The Society for Investigative Dermatology, Inc., United States (2001).

Vandermeeren, M., et al., "Dimethylfumarate Is an Inhibitor of Cytokine-Induced E-Selection, VCAM-1, and ICAM-1 Expression in Human Endothelial Cells," *Biochem. Biophys. Res. Comm.* 234:19-23, Academic Press, United States (1997).

Wang, X., et al., "Enhanced cytotoxicity of mitomycin C in human tumour cells with inducers of DT-diaphorase," *British Journal of Cancer* 80:1223-1230, Cancer Research Campaign, England (1999).

Weinmann, I., et al., "Influence of Fumaric Acid Derivates on T Lymphocytes in The Murine Model of HSV-1 Keratitis," *Invest. Opthalmol. Vis. Sci.* 41(4):S146, Association for Research in Vision and Ophthalmology annual meeting, Fort Lauderdale, Florida, United States, Apr. 30-May 5, 2000, United States (2000) (Abstract Only).

International Preliminary Examination Report for International Application No. PCT/EP99/08215, completed Feb. 27, 2001.

Office Action mailed Oct. 2, 2009, in U.S. Appl. No. 12/405,661, Joshi, R.K., et al., filed Mar. 17, 2009 (now U.S. Patent No. 7,803,840 B2).

Preliminary Amendment filed Jun. 20, 2007, in U.S. Appl. No. 11/765,563, Joshi, R.K., et al., filed Jun. 20, 2007 (now U.S. Patent No. 7,612,110 B2).

Supplemental Preliminary Amendment filed Oct. 19, 2007, in U.S. Appl. No. 11/765,563, Joshi, R.K., et al., filed Jun. 20, 2007 (now U.S. Patent No. 7,612,110 B2).

Office Action mailed Dec. 3, 2007, in U.S. Appl. No. 11/765,563, Joshi, R.K., et al., filed Jun. 20, 2007 (now U.S. Patent No. 7,612,110 B2).

Final Office Action mailed Sep. 9, 2008, in U.S. Appl. No. 11/765,563, Joshi, R.K., et al., filed Jun. 20, 2007 (now U.S. Patent No. 7,612,110 B2).

Response filed Jun. 3, 2008, in U.S. Appl. No. 11/765,563, Joshi, R.K., et al., filed Jun. 20, 2007 (now U.S. Patent No. 7,612,110 B2).

Notice of Allowance mailed Jun. 12, 2009 in U.S. Appl. No. 11/765,563, Joshi, R.K., et al., filed Jun. 20, 2007 (now U.S. Patent No. 7,612,110 B2).

Office Action mailed Mar. 22, 2004, in U.S. Appl. No. 10/197,077, Joshi, R.K., et al., filed Jul. 17, 2002 (now U.S. Patent No. 7,320,999 B2).

Response filed Aug. 6, 2004, in U.S. Appl. No. 10/197,077, Joshi, R.K., et al., filed Jul. 17, 2002 (now U.S. Patent No. 7,320,999 B2).

Notice of Non-compliant Amendment mailed Aug. 19, 2004, in U.S. Appl. No. 10/197,077, Joshi, R.K., et al., filed Jul. 17, 2002 (now U.S. Patent 7,320,999).

Response filed Aug. 25, 2004, in U.S. Appl. No. 10/197,077, Joshi, R.K., et al., filed Jul. 17, 2002 (now U.S. Patent No. 7,320,999 B2).

Supplemental Amendment filed Nov. 22, 2004, in U.S. Appl. No. 10/197,077, Joshi, R.K., et al., filed Jul. 17, 2002 (now U.S. Patent No. 7,320,999 B2).

Notice of Non-compliant Amendment mailed Dec. 16, 2004, in U.S. Appl. No. 10/197,077, Joshi, R.K., et al., filed Jul. 17, 2002 (now U.S. Patent No. 7,320,999 B2).

Response to Notice of Non-compliant Amendment filed Jan. 5, 2005, in U.S. Appl. No. 10/197,077, Joshi, R.K., et al., filed Jul. 17, 2002 (now U.S. Patent No. 7,320,999 B2).

Office Action mailed Nov. 28, 2005, in U.S. Appl. No. 10/197,077, Joshi, R.K., et al., filed Jul. 17, 2002 (now U.S. Patent No. 7,320,999 B2).

Response filed Feb. 24, 2006, in U.S. Appl. No. 10/197,077, Joshi, R.K., et al., filed Jul. 17, 2002 (now U.S. Patent No. 7,320,999 B2).

Notice of Non-compliant Amendment mailed Mar. 1, 2006, in U.S. Appl. No. 10/197,077, Joshi, R.K., et al, filed Jul. 17, 2002 (now U.S. Patent No. 7,320,999 B2).

Response to Notice of Non-compliant Amendment filed Mar. 10, 2006, in U.S. Appl. No. 10/197,077, Joshi, R.K., et al., filed Jul. 17, 2002 (now U.S. Patent No. 7,320,999 B2).

Office Action mailed Jun. 21, 2006, in U.S. Appl. No. 10/197,077, Joshi, R.K., et al., filed Jul. 17, 2002 (now U.S. Patent No. 7,320,999 B2).

Response to Restriction Requirement dated Jun. 21, 2006, filed Aug. 21, 2006, in U.S. Appl. No. 10/197,077, Joshi, R.K., et al., filed Jul. 17, 2002 (now U.S. Patent No. 7,320,999 B2).

Amendment filed Mar. 2, 2007, in U.S. Appl. No. 10/197,077, Joshi, R.K., et al., filed Jul. 17, 2002 (now U.S. Patent No. 7,320,999 B2).

Office Action mailed May 15, 2007, in U.S. Appl. No. 10/197,077, Joshi, R.K., et al., filed Jul. 17, 2002 (now U.S. Patent No. 7,320,999 B2).

Interview Summary for interview held Aug. 7, 2007, in U.S. Appl. No. 10/197,077, Joshi, R.K., et al., filed Jul. 17, 2002 (now U.S. Patent No. 7,320,999 B2).

Amendment filed Aug. 15, 2007, in U.S. Appl. No. 10/197,077, Joshi, R.K., et al., filed Jul. 17, 2002 (now U.S. Patent No. 7,320,999 B2).

Notice of Allowance mailed Aug. 28, 2007, in U.S. Appl. No. 10/197,077, Joshi, R.K., et al., filed Jul. 17, 2002 (now U.S. Patent No. 7,320,999 B2).

Preliminary Amendment filed May 10, 2001, in U.S. Appl. No. 09/831,620, Joshi, R.K., et al., § 371(c) date May 10, 2001 (now U.S. Patent No. 6,509,376 B1).

Office Action mailed Dec. 7, 2001, in U.S. Appl. No. 09/831,620, Joshi, R.K., et al., § 371(c) date May 10, 2001 (now U.S. Patent No. 6,509,376 B1).

Response filed Dec. 31, 2001, in U.S. Appl. No. 09/831,620, Joshi, R.K., et al., § 371(c) date May 10, 2001 (now U.S. Patent No. 6,509,376 B1).

Office Action mailed Mar. 4, 2002, in U.S. Appl. No. 09/831,620, Joshi, R.K., et al., § 371(c) date May 10, 2001 (now U.S. Patent No. 6,509,376 B1).

Response filed May 20, 2002, in U.S. Appl. No. 09/831,620, Joshi, R.K., et al., § 371(c) date May 10, 2001 (now U.S. Patent No. 6,509,376 B1).

Notice of Allowance mailed Aug. 30, 2002, in U.S. Appl. No. 09/831,620, Joshi, R.K., et al., § 371(c) date May 10, 2001 (now U.S. Patent No. 6,509,376 B1).

Office Action mailed Mar. 12, 2009, in U.S. Appl. No. 11/765,563, Joshi, R.K., et al., filed Jun. 20, 2007 (now U.S. Patent No. 7,612,110 B2).

Office Action mailed Dec. 14, 2007, in U.S. Appl. No. 11/765,578, Joshi, R.K., et al., filed Jun. 20, 2007 (now U.S. Patent No. 7,619,001 B2).

Office Action mailed Jul. 25, 2008, in U.S. Appl. No. 11/765,578, Joshi, R.K., et al., filed Jun. 20, 2007 (now U.S. Patent No. 7,619,001 B2).

Office Action mailed Sep. 15, 2008, in U.S. Appl. No. 11/765,578, Joshi, R.K., et al., filed Jun. 20, 2007 (now U.S. Patent No. 7,619,001 B2).

Office Action mailed Mar. 30, 2009, in U.S. Appl. No. 11/765,578, Joshi, R.K., et al., filed Jun. 20, 2007 (now U.S. Patent No. 7,619,001 B2).

Notice of Allowance and Fees Due mailed Jun. 17, 2009, in U.S. Appl. No. 11/765,578, Joshi, R.K., et al., filed Jun. 20, 2007 (now U.S. Patent No. 7,619,001 B2).

Office Action mailed Jan. 19, 2010, in U.S. Appl. No. 12/405,661, Joshi, R.K., et al., filed Mar. 17, 2009 (now U.S. Patent No. 7,803,840 B2).

Office Action mailed May 20, 2010, in U.S. Appl. No. 12/405,661, Joshi, R.K., et al., filed Mar. 17, 2009 (now U.S. Patent No, 7,803,840 B2).

Notice of Allowance and Fees Due mailed Jul. 13, 2010, in U.S. Appl. No. 12/405,661, Joshi, R.K., et al., filed Mar. 17, 2009 (now U.S. Patent No. 7,803,840 B2).

Office Action mailed Mar. 23, 2010, in U.S. Appl. No. 12/405,665, Joshi, R.K., et al., filed Mar. 17, 2009 (now U.S. Patent No. 7,915,310 B2).

Office Action mailed Sep. 9, 2010, in U.S. Appl. No. 12/405,665, Joshi, R.K., et al., filed Mar. 17, 2009 (now U.S. Patent No. 7,915,310 B2).

Notice of Allowance and Fees Due mailed Nov. 24, 2010, in U.S. Appl. No. 12/405,665, Joshi, R.K., et al., filed Mar. 17, 2009 (now U.S. Patent No. 7,915,310 B2).

English language excerpt from Hunziker, T. and Schmidli, J., "Is Psoriasis an Autoimmune Disease?" *Therapeutische Umschau* 50:110-113, Dermatologische Klinik der Universität Bern, Switzerland (1993).

English language translation of Mrowietz, U., "Nephrotoxische Wirkung durch Fumarsäure," *Hautarzt* 51:615, Springer-Verlag, Germany (2000).

English Language Translation of German Patent Publication No. DE 28 40 498 B1 (1979) (listed as document FP35 on the accompanying PTO/SB/08/A form).

English language Abstract of Japanese Patent Publication No. JP 9-221428 A, European Patent Office, espacenet database—Worldwide (2010) (listed as document FP36 on the accompanying form PTO/SB/08A).

Anderson, et al., "Aetiology of Multiple Sclerosis," *British Medical Journal* 1(5433):466-467, British Medical Association, England (1965).

"Polyarthritis," Wikipedia.org, accessed at www.en.wikipedia.org/wiki/Polyarthritis, accessed on Sep. 3, 2008, 4 pages.

Roitt, I.M., et al., eds., "23 Autoimmunity and Autoimmune Disease," in *Immunology*, p. 23.1-23.12, Gower Medical Publishing, United States (1985).

Wright, R., "Autoimmune disease of the gastro-intestinal tract," *Postgrad. med. J.* 44:765-768, Blackwell, England (1968).

English language translation of Altmeyer, P. and Nüchel, C., "Systemtherapie der Psoriasis," *Dtsch. med. Wschr.* 121:1605-1607, Georg Thieme Verlag, Germany (1996).

English Language Translation of German Patent Publication No. DT 26 21 214 (corresponding to FP4 on corresponding PTO/SB08/A form).

English language Abstract of German Patent Publication No. DE 38 34 794 A1, European Patent Office, espacenet database—Worldwide (2010) (listed as document FP6 on the accompanying form PTO/SB/08A).

"Design for Pharmaceutical Preparations for oral administration," Kabushiki Kaisha Yakugyo Jihosha, p. 312-317 (1995).

English language translation of "Design for Pharmaceutical Preparations for oral administration," Kabushiki Kaisha Yakugyo Jihosha, p. 312-317 (1995).

Lahti, A., et al., "Acetylsalicylic acid inhibits non-immunologic contact urticaria," *Contact Dermatitis* 16:133-135, Munksgaard International Publishers Ltd., Denmark (1987).

Werdenberg, D., *Stability, Permeability and Pharmacokinetics of Perorally Administered Fumarates*, Doctoral Dissertation submitted to the Swiss Federal Institute of Technology Zurich, pp. 86, 87, 90, 125 (2003).

English language Abstract of International Patent Publication No. WO 2005/027899 A1, European Patent Office, espacenet database—Worldwide (2005) (listed as document FP29 on the accompanying form PTO/SB/08A).

English Language Translation of Sadjak, A. et al., "Nephrotoxische Wirkung von Fumarsaurederivaten," *Deutsch Med. Wochenschr.* 116:478, G. Thieme, Germany (1991).

Dialog File 351, Accession No. 1266465, Derwent WPI English language abstract for DT 25 30 372 A1 (1977) (listed as document FP3 on accompanying form PTO/SB/08A).

Co-pending, U.S. Appl. No. 13/465,740, inventor Lukashev, M., filed May 7, 2012 (Not Published).

Co-pending, U.S. Appl.No. 13/578,430, inventor Goelz et al., filed Feb. 11, 2011 (Not Published).

Kolbach, D.N. and Niebor, C., "Fumaric acid therapy in psoriasis: a long-term retrospective study on the effect of fumaric acid combination (FAC-EC) therapy and dimethyl-fumaric acid ester (DMFAE) monotherapy," *British Journal of Dermatology* 123:534-535, Blackwell Scientific Publications, England (1990).

Office Action mailed Aug. 20, 2012, in U.S. Appl. No. 12/884,573, Joshi et al., filed Sep. 17, 2010.

Office Action mailed Jul. 13, 2011, in U.S. Appl. No. 12/526,296, Lukashev et al., §371(c) date Jan. 13, 2011.

Office Action mailed Dec. 15, 2011, in U.S. Appl. No. 12/526,296, Lukashev et al., §371(c) date Jan. 13, 2011.

Office Action mailed May 3, 2012, in U.S. Appl. No. 13/372,426, Lukashev, filed Feb. 13, 2012.

Office Action mailed Aug. 28, 2012, in U.S. Appl. No. 13/465,740, Lukashev, filed May 7, 2012.

Office Action mailed Mar. 20, 2012, in U.S. Appl. No. 12/525,805, Gold, §371(c) date Feb. 1, 2010.

Office Action mailed Mar. 23, 2004, in U.S. Appl. No. 10/148,858, Joshi et al., §371(c) date May 28, 2002 (now U.S. Patent No. 6,858,750).

Office Action mailed Aug. 12, 2003, in U.S. Appl. No. 10/148,858, Joshi et al., §371(c) date May 28, 2002 (now U.S. Patent No. 6,858,750).

Office Action mailed Feb. 12, 2007, in U.S. Appl. No. 10/250,983, Joshi et al., §371(c) date Jul. 10, 2003 (now abandoned).

Office Action mailed Jul. 20, 2006, in U.S. Appl. No. 10/250,983, Joshi et al., §371(c) date Jul. 10, 2003 (now abandoned).

Office Action mailed Nov. 14, 2008, in U.S. Appl. No. 11/833,150, Joshi et al., filed Aug. 2, 2007 (now abandoned).

Office Action mailed Jan. 10, 2006, in U.S. Appl. No. 10/433,295, Joshi et al., §371(c) date Jun. 2, 2003 (now Patent No. 7,157,423).

Office Action mailed Apr. 22, 2005, in U.S. Appl. No. 10/433,295, Joshi et al., §371(c) date Jun. 2, 2003 (now Patent No. 7,157,423).

Office Action mailed Sep. 9, 2004, in U.S. Appl. No. 10/433,295, Joshi et al., §371(c) date Jun. 2, 2003 (now Patent No. 7,157,423).

Office Action mailed Dec. 14, 2007, in U.S. Appl. No. 11/421,083, Joshi et al., filed May 31, 2006 (now U.S. Patent No. 7,432,240).

Office Action mailed May 8, 2007, in U.S. Appl. No. 11/421,083, Joshi et al., filed May 31, 2006 (now U.S. Patent No. 7,432,240).

Office Action mailed Nov. 25, 2009, in U.S. Appl. No. 10/511,564, Joshi et al., §371(c) date Oct. 15, 2004 (now Patent No. 7,790,916).

Office Action mailed Apr. 3, 2009, in U.S. Appl. No. 10/511,564, Joshi et al., §371(c) date Oct. 15, 2004 (now Patent No. 7,790,916).

Office Action mailed Aug. 11, 2008, in U.S. Appl. No. 10/511,564, Joshi et al., §371(c) date Oct. 15, 2004 (now Patent No. 7,790,916).

Office Action mailed Apr. 10, 2008, in U.S. Appl. No. 10/511,564, Joshi et al., §371(e) date Oct. 15, 2004 (now Patent No. 7,790,916).

Office Action mailed Oct. 1, 2007, in U.S. Appl. No. 10/511,564, Joshi et al., §371(c) date Oct. 15, 2004 (now Patent No. 7,790,916).

Office Action mailed Apr. 9, 2007, in U.S. Appl. No. 10/511,564, Joshi et al., §371(c) date Oct. 15, 2004 (now Patent No. 7,790,916).

Office Action mailed Apr. 26, 2000, in U.S. Appl. No. 09/194,862, Joshi et al., §371(c) date Apr. 1, 1998 (now U.S. Patent 6,436,992).

Office Action mailed Oct. 31, 2000, in U.S. Appl. No. 09/402,103, Joshi et al., §371(c) date Dec. 8, 1998 (now U.S. Patent 6,277,882).

Office Action mailed May 21, 2001, in U.S. Appl. No. 09/743,978, Joshi et al., §371(c) date Oct. 8, 1999 (now U.S. Patent 6,355,676).

Balashov, K.E., et al., "Increased interleukin 12 production in progressive multiple sclerosis: Induction by activated CD4+T cells via CD40 ligand," *Proc. Natl. Acad. Sci.* 94:559-603, National Academy of Sciences, United States (1997).

Bista, P., et al. "Dimethyl Fumarate Suppresses Inflammation In Vitro via Both Nrf2-Dependent and Nrf2-Independent Pathways," *64th Annual Meeting of the American Academy of Neurology*, 1 page poster, United States (2012).

"BG 12—BG 00012, BG 12/Oral Fumarate, FAG-201, Second Generation Fumarate Derivative—Fumapharm/Biogen Idec," *Drug R. D.* 6(4):229-230, Adis Data Information B.V., Netherlands (2005).

Kappos, L., et al., "Efficacy and safety of oral fumarate in patients with relapsing-remitting multiple sclerosis: a multicentre, randomised, double-blind, placebo-controlled phase IIb study," *Lancet* 372:1463-1472, Lancet Publishing Group, England (2008).

Kappos, L., et al., "The Efficacy of BG00012 in Patients With Relapsing-Remitting Multiple Sclerosis: Subgroup Analyses From the Phase 2b Study," *50th Annual Meeting of the American Academy of Neurology*, 7 pages, United States (2008).

Mrowietz, U., et al., "Treatment of severe psoriasis with fumaric acid esters: scientific background and guidelines for therapeutic use," *British Journal of Dermatology* 141:424-429, British Association of Dermatologists, England (1999).

Wierinckx, A., "Detoxication enzyme inducers modify cytokine production in rat mixed glial cells," *J. Neuroimmun.* 166:132-143, Elsevier B.V., Netherland (2005).

Office Action mailed Nov. 26, 2012 in U.S. Appl. No. 13/040,914, Joshi, R. K., et al., filed Mar. 4, 2011.

\* cited by examiner

UTILIZATION OF DIALKYLFUMARATES

REFERENCE TO RELATED APPLICATIONS

This application is a divisional application U.S. application Ser. No. 13/040,914, filed on Mar. 4, 2011, which is a continuation application of U.S. application Ser. No. 12/405,665, filed on Mar. 17, 2009, and issued as U.S. Pat. No. 7,915,310 B 2. U.S. application Ser. No. 12/405,665, filed on Mar. 7,2009, is a continuation application of U.S. application Ser. No. 11/765,578, filed on Jun. 20, 2007, and issued as U.S. Pat. No. 7,619,001 B2. U.S. application Ser. No. 11/765,578, filed on Jun. 20, 2007, is a continuation application of U.S. Application No. 10/197,077, filed on Jul. 17, 2002, and issued as U.S. Pat. No. 7,320,999 B 2. U.S. application Ser. No. 10/197, 077, files on Jul. 17, 2002, is a divisional application of U.S. application Ser. No. 09/831,620, filed May 10, 2001, and issued as U.S. Pat. No. 6,509,376 B 1. U.S. application Ser. No. 09/831,620, filed May 10, 2001, is a 371 continuation of PCT Application PCT/EP99/08215, filed Oct. 29, 1999, the text of which is not in English, which PCT Application claims priority on German Application No. 198 53 487.6, filed Nov. 19, 1998, the text of which is not in English.

DESCRIPTION

The present invention relates to the use of dialkyl fumarates for preparing pharmaceutical preparations for use in transplantation medicine or the therapy of autoimmune diseases and pharmaceutical preparations in the form of micro-tablets or micro-pellets containing dialkyl fumarates.

On the one hand, therefore, it relates especially to the use of dialkyl fumarates for preparing pharmaceutical preparations for the treatment, reduction or suppression of rejection reactions of the transplant by the recipient, i.e. host-versus graft reactions, or rejection of the recipient by the transplant, i.e. graft-versus-host reactions. On the other hand, it relates to the use of dialkyl fumarates for preparing pharmaceutical preparations for treating autoimmune diseases such as polyarthritis, multiple sclerosis, juvenile-onset diabetes, Hashimoto's thyroiditis, Grave's disease, systemic Lupus erythematodes (SLE), Sjogren's syndrome, pernicious anaemia and chronic active lupoid) hepatitis.

Both graft rejection and autoimmune diseases are based on medically undesirable reactions or dysregulation of the immune system. Cytokins such as interleukins or tumour necrose factor α (TNF-α) are substantial mediators influencing the immune system. In general, both are treated by the administration of immunosuppressive agents such as cyclosporine.

In the overall result, autoimmune diseases may be defined as the failure of the tolerance of endogenic substances or antigens. As a rule, this tolerance can be maintained only if the antigens keep coming into contact with immunological cells. When this tolerance is lost, autoantibodies are formed, i.e. a humoral immunoresponse against endogenic tissue. The exact nature of the involvement of TNF-α is not known.

Transplantations are tissue or organ transplantations, Le. the transfer of tissues such as cornea, skin, bones (bone chips), vessels or fasciae, of organs such as kidney, heart, liver, lung, pancreas or intestines, or of individual cells such as islet cells, α-cells and liver cells, the kidney having the greatest significance as a transplanted organ.

According to the degree of relationship between the donor and the recipient we differentiate between autotransplantation (transfer to another part of the body of the same individual), iso-transplantation (transfer to another, genetically identical individual) and allogenic transplantation (transfer to another individual of the same species). Depending on the site of origin and transplantation, we further differentiate between homotopic transplantation (transfer to the same site) and heterotopic transplantation (transfer to a different site). The above-mentioned transplantations play an important role in modem medicine.

A major problem in transplantation medicine is graft rejection after transplantation of the tissue, organ, or cell by immunological defense reactions of the recipient. Such a graft rejection is also called host-versus-graft reaction. The immunological defense reaction of the organism against the heteroprotein often results in rejection or dissolution of the grafts. In host-verses-graft reactions, different stages may be distinguished. Depending on the degree of difference between the recipient and the donor, this reaction takes place at different speeds so that we speak of an acute, sub-acute or chronic reaction. The acute rejection process is accompanied by the irreversible loss of the transplant (necrotisation) as a result of arteriitis or arteriolitis within 48 hours and cannot be influenced by the administration of drugs. The sub-acute rejection reaction becomes manifest as a rejection crisis from day 12 to month 4 with reversible functional disorders as a result of a transplant vasculopathy. Finally, the loss of function of the transplant as a result of vascular changes such as obliterating arteriopathy, which proceeds over weeks or years and can practically not be influenced by drugs, is termed a chronic rejection reaction.

Vice-versa, rejection reactions of the transplant against the recipient, the so-called graft-versus-host reactions, may occur when immunocompetent tissues are transplanted, i.e. primarily in bone marrow transplantation. Again, the severity of the reaction is graded, and substantially similar complications result as in host-versus-graft-reactions, namely arteriopathies and necroses.

To avoid such rejection reactions, i.e. the host-versus-graft reaction and the graft-versus-host reaction, transplantation medicine essentially makes use of immunosuppression, Le. a weakening of the normal immunoresponse. For this purpose, anti-lymphocyte sera are often used in combination with corticosteroids and so-called anti-metabolites, e.g. purine analogues such as 6-mercaptopurine and thioguanine which affect the nucleic acid and protein synthesis and thus prevent cell division and proliferation. This leads to suppression of the production of antibodies and the cellular immune response. The immunosuppressive agents used for therapy are substances which suppress or weaken the immunoreaction in the body either specifically or non-specifically. Non-specific immunosuppressive agents are cytostatic agents such as, for example, alkylating agents or antimetabolites.

In addition, active ingredients are known which cause at least partial specific immunosuppression, such as corticosteroids, antisera, antibodies FK-506, tacrolimus, mycophenolatemofeta and primarily cyclosporines such as cyclosporine A. a result of using modem immunosuppressive agents, the most important representatives of which are the cyclosporines, especially cyclosporine A, it was possible to improve the results of transplantation considerably over the last few years. At present, the survival rate after one year is about 60% for liver transplantations, about 80% for heart transplantations and over 90% for kidney transplantations.

Autoimmune diseases where the endogenic immune system attacks endogenic organs, tissues and cells are comparable to graft-versus-host reactions. These are also medically undesirable reactions of the immune system which may be treated with immunosuppressive agents, too.

The danger in using immunosuppressive agents lies in weakening the body's defense against infectious diseases and the increased risk of malignant diseases. Therefore, it is the object of the invention to provide a pharmaceutical preparation to be employed in transplantation medicine which may be used to treat, especially to suppress, weaken and/or alleviate host-versus-graft reactions and graft-versus-host reactions, but does not have the above disadvantage.

It is another object of the invention to provide a pharmaceutical preparation which may be employed for treating autoimmune diseases, particularly polyarthritis, multiple sclerosis, juvenile-onset diabetes, Hashimoto's thyroiditis, Grave's disease, systemic Lupus erythematodes (SLE), Sjogren's syndrome, pernicious anaemia and chronic active (=lupoid) hepatitis, without the disadvantages of immunosuppression.

The object of the invention is achieved by using certain dialkyl fumarates for preparing pharmaceutical preparations for use in transplantation medicine and for the therapy of autoimmune diseases and pharmaceutical preparations in the form of micro-tablets and micro-pellets containing these dialkyl fumarates. The individual subject matters of the invention are characterized in detail in the claims. The preparations according to the invention do not contain any free fumaric acids per se.

It is known that pharmaceutical preparations which, upon biological degradation after administration, enter into the citric acid cycle or are part thereof gain increasing therapeutic significance—especially when given in high dosages—since they can alleviate or heal diseases caused cryptogenetically.

Fumaric acid, for example, inhibits the growth of the Ehrlich ascites tumour in mice, reduces the toxic effects of mitomycin C and aflatoxin and displays antipsoriatic and antimicrobial activity. When administered parenterally, transdermally and especially perorally, high dosages of fumaric acid or its derivatives known so far such as dihydroxyl fumaric acid, fumaramide and fumaronitrile have such unacceptably severe side effects and high toxicity that, in most cases, such a therapy had to be abandoned in the past.

Surprisingly, investigations carried out by the applicant have shown that methyl hydrogen fumarate, a metabolite of the dimethyl fumarate, initially increases the endotoxin-stimulated TNF-α secretion in human mononuclear cells of periphere blood (periphere blood mononuclear cells=PBMC cells) and in isolated monocytes. In addition, the applicant was able to show that fumaric acid has an effect on in vitro and in vivo haemagglutination which is comparable to that of cyclosporine.

Surprisingly, it has now been found that dialkyl fumarates are advantageous for preparing pharmaceutical compositions for use in transplantation medicine and for the therapy of autoimmune diseases. This is because compositions containing such dialkyl fumarates surprisingly permit a positive modulation of the immune system in host-versus-graft reactions, graft-versus-host reactions and other autoimmune diseases.

European Patent Application 0188 749 already describes fumaric acid derivatives and pharmaceutical compositions containing the same for the treatment of psoriasis. Pharmaceutical compositions for the treatment of psoriasis containing a mixture of fumaric acid and other fumaric acid derivatives are known from DE-A-25 30 372. The content of free fumaric acid is obligatory for these medicaments.

DE-A-26 21 214 describes medicaments containing the fumaric acid monoethyl ester and its mineral salts as active ingredient for the treatment of psoriasis. The publication "Hautarzt (*Dermatologist*) (1987) 279-285" discusses the use of fumaric acid monoethyl ester salts. Pharmaceutical preparations containing a mixture of fumaric acid monoalkyl ester salts and a fumaric acid diester for the treatment of psoriasis, psoriatic arthritis, neurodermatitis and enteritis regionalis Crohn are known from EP 0 312 697 B1.

Specifically, the object of the invention is achieved by the use of one or more dialkyl fumarates of the formula

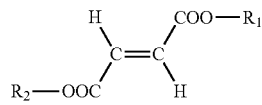

wherein $R_1$ and $R_2$, which may be the same or different, independently represent a linear, branched or cyclic, saturated or unsaturated $C_{1-20}$ alkyl radical which may be optionally substituted with halogen (Cl, F, I, Br), hydroxy, alkoxy, nitro or cyano for preparing a pharmaceutical preparation for use in transplantation medicine or for the therapy of autoimmune diseases.

The $C_{1-20}$ alkyl radicals, preferably $C_{1-8}$ alkyl radicals, most preferably $C_{1-5}$ alkyl radicals are, for example, methyl, ethyl, n-propyl, isopropyl, n-butyl, sec-butyl, t-butyl, pentyl, cyclopentyl, 2-ethyl hexyl, hexyl, cyclohexyl, heptyl, cycloheptyl, octyl, vinyl, allyl, 2-hydroxyethyl, 2 or 3-hydroxy propyl, 2-methoxy ethyl, methoxy methyl or 2- or 3-methoxy propyl. Preferably at least one of the radicals or $R_2$ is $C_{1-5}$ alkyl, especially methyl or ethyl. More preferably, $R_1$ and $R_2$ are the same or different $C_{1-5}$ alkyl radicals such as methyl, ethyl, n-propyl or t-butyl, methyl and ethyl being especially preferred. Most preferably, $R_1$ and $R_2$ are identical and are methyl or ethyl. Especially preferred are the dimethyl fumarate, methyl ethyl fumarate and diethyl fumarate.

The dialkyl fumarates to be used according to the invention are prepared by processes known in the art (see, for example, EP 0 312 697).

Preferably, the active ingredients are used for preparing oral preparations in the form of tablets, micro-tablets, pellets or granulates, optionally in capsules or sachets. Preparations in the form of micro-tablets or pellets, optionally filled in capsules or sachets are preferred and are also a subject matter of the invention. The oral preparations may be provided with an enteric coating. Capsules may be soft or hard gelatine capsules.

The dialkyl fumarates used according to the invention may be used alone or as a mixture of several compounds, optionally in combination with the customary carriers and excipients. The amounts to be used are selected in such a manner that the preparations obtained contain the active ingredient in an amount corresponding to 10 to 300 mg of fumaric acid.

Preferred preparations according to the invention contain a total amount of 10 to 300 mg of dimethyl fumarate and/or diethyl fumarate.

According to a preferred embodiment, the size or the mean diameter, respectively, of the pellets or micro-tablets is in the range from 300 to 2,000 μm, especially in the range of 500 or 1,000 μm.

In addition to graft-versus-host reactions (see above), the following autoimmune diseases to be treated may be named: polyarthritis, multiple sclerosis, graft-versus-host reactions, juvenile-onset diabetes, Hashimoto's thyroiditis, Grave's disease, systemic Lupus erythernatodes (SLE), Sjogren's syndrome, pernicious anaemia and chronic active (lupoid)

hepatitis. Autoimmune diseases in a wider meaning also comprise psoriasis, psoriatic arthritis, neurodermatitis and enteritis regionalis Crohn.

In addition to the preparations for peroral administration in the form of micro-pellets, micro-tablets, capsules (such as soft and hard gelatine capsules), granulates and tablets cited above, suitable pharmaceutical preparations are preparations for cutaneous and transdermal administration in the form of ointments, plasters, lotions or shower preparations and for parenteral administration in the form of aqueous micro-dispersions, oil-in-water emulsions or oily solutions for rectal administration of suppositories or micro-enemas. Pharmaceutical preparations in the form of micro-tablets or micro-pellets are preferred for the therapy of all autoimmune diseases mentioned above, including psoriasis, psoriatic arthritis, neurodermatitis and enteritis regionalis Crohn and are also a subject matter of the invention.

According to the invention, a therapy with dialkyl fumarates may also be carried out in combination with one or more preparations of the triple drug therapy customarily used in organ transplantations or with cyclosporine A alone. For this purpose, the preparations administered may contain a combination of the active ingredients in the known dosages or amounts, respectively. Likewise, the combination therapy may consist of the parallel administration of separate preparations, by the same or different routes. Optionally, the dosage of the active ingredient contained in addition to the dose of the fumaric acid derivative administered in accordance with the invention may be reduce4 advantageously.

Another embodiment of the use according to the invention is to alternate the drug therapy with immunosuppressive agents such as cyclosporine in sequence with an application of the above-mentioned dialkyl furnarate. This means that an application of fumaric acid derivatives as defined above over one or more weeks may follow a cyclosporine therapy of one or more weeks. This permits reduction of the Cyclosporine A dosage resulting in a considerable decrease of the rate of side effects in long-term therapy.

By administration of the dialkyl fumarates in the form of micro-tablets, which is preferred, gastrointestinal irritations and side effects, which are reduced already when conventional tablets are administered but is still observed, may be further reduced vis-a-vis fumaric acid derivatives and salts.

It is presumed that, upon administration of conventional tablets, the ingredients of the tablet are released in the intestine in a concentration which is too high, causing local irritation of the intestinal mucous membrane. This local irritation results in a short-term release of very high TNF-α concentrations which may be responsible for the gastrointestinal side effects. in case of application of enteric-coated micro-tablets in capsules, on the other hand, very low local concentrations of the active ingredients in the intestinal epithelial cells are achieved. The micro-tablets are incrementally released by the stomach and passed into the small intestine by peristaltic movements so that distribution of the active ingredients is improved.

This means that enteric-coated micro-tablets in the same dosage are distributed already in the stomach and passed to the intestine in portions, where the active ingredients are released in smaller dosages. This avoids local irritation of the intestinal epithelial cells and the release of TNF-α. It is assumed that this results in the improved tolerance of micro-tablets in the gastrointestinal tract vis-a-vis conventional tablets.

In addition, resorption is improved, because the dialkyl fumarates to be used according to the invention are not the active ingredient per se, but a so-called prodrug, which must be converted into the active ingredient in the body.

In order to illustrate the use according to the invention, different examples for preparing preferred drugs are given below.

PRODUCTION EXAMPLES

In principle, the oral preparations according to the invention in the form of tablets or micro-tablets may be prepared by classical tabletting processes. Instead of such classical tabletting processes, other methods for the preparation of tablets may be used, such as direct tabletting and processes for preparing solid dispersions in according with the melt method and the spray drying method.

The tablets may be provided with an enteric coating. The enteric coating may be applied in a classical coating pan or sprayed on or applied in a fluidised bed apparatus. The tablet may also be provided with a film coat.

Example 1

Preparation of Enteric-coated Micro-tablets in Capsules Containing 120.0 mg of Dimethyl Fumarate, which Corresponds to 96 mg of Fumaric Acid Taking the necessary precautions (breathing mask, gloves, protective clothing, etc.), 12.000 kg of dimethyl fumarate are crushed, mixed and homogenized by means of a sieve 800. Then an excipient mixture with the following composition is prepared: 17.50 kg of starch derivative (STA-RX® 1500), 0.30 kg of microcrystalline cellulose (Avicel® PH 101), 0.75 kg of PVP (Kollidon® 120), 4.00 kg of Primogel®, 0.25 kg of colloidal silicic acid (Aerosil®). The active ingredient is added to the entire powder mixture, mixed, homogenized by means of a sieve 200, processed in the usual manner with a 2% aqueous solution of polyvidon pyrrolidone (Kollidon® K25) to obtain a binder granulate and then mixed in the dry state with the outer phase. Said outer phase consists of 0.50 kg of Mg stearate and 1.50 kg of talcum.

Then the powder mixture is compressed in the usual manner to obtain convex tablets having a gross weight of 10.0 mg and a diameter of 2.0 mm.

One example to achieve resistance to gastric acid is to dissolve a solution of 2.250 kg of hydroxy propyl methyl cellulose phthalate (HPMCP, Pharmacoat® HP 50) in portions in a mixture of the following solvents: 13.00 l of acetone, 13.50 l of ethanol (94 wt.-%, denatured with 2% of ketone) and 1.50 l of demineralised water, As a plasticiser castor oil (0.240 kg) is added to the finished solution and applied in portions onto the tablet cores in the customary manner.

After drying is completed, a suspension of the following composition is applied as a film coat in the same apparatus: 0.340 kg of talcum, 0.400 kg of titanium (VI) oxide Cronus RN 56, 0.324 kg of coloured lacquer L-Rot-lack 86837, 4.800 kg of Eudragit E 12.5% and 0.120 kg of polyethylene glycol 6000. pH 11 XI in a solvent mixture of the following composition: 8.170 kg of 2-propanol, 0.200 kg of demineralised water and 0.600 kg of glycerine triacetate (Triacetin).

After that the enteric-coated micro-tablets are filled into hard gelatine capsules having a net weight of 400 mg and sealed.

Example 2

Preparation of Enteric-coated Micro-tablets in Capsules Containing 120.0 mg of Dimethyl Fumarate, which Corresponds to 96 mg of Fumaric Acid 12.000 kg of dimethyl fumarate are crushed end homogenized as above. Then an excipient mixture composed as follows is prepared: 23.20 kg of microcrystalline cellulose (Avicel® PH 200), 3.00 kg of Croscarmellose sodium (AC-Di-SOL-SD-711), 2.50 kg of talcum, 0.10 kg of anhydrous silica (Aerosil® 200) and 1.00 kg of Mg stearate. The active ingredient is then added to the entire powder mixture and mixed homogenously. By means of direct tabletting, the powder mixture is then pressed into convex tablets having a gross weight of 10.0 mg and a diameter of 2.00 mm.

After that, a solution of 0.94 Eudragit® L in isopropanol is prepared which also contains 0.07 kg of dibutyl phthalate. This solution is sprayed onto the tablet cores. After that, a dispersion of 17.32 kg of Eudragit® L D-55 and a mixture of 2.80 kg of microtalcum, 2.00 kg of Macrogol 6000 and 0.07 kg of dimeticon in water is prepared and sprayed onto the cores.

Next, the enteric-coated micro-tablets are filled into hard gelatine capsules having a net weight of 650 mg and sealed.

Example 3

Preparation of Micro-pellets in Capsules Containing 50.0 mg of Dimethyl Fumarate, which Corresponds to 40 mg of Fumaric Acid 5.000 kg of dimethyl fumarate are crushed and homogenized as above. In addition, 2 l of a 20% (m/v) polyvinyl pyrrolidone solution (Kollidon K-30) in ethanol are prepared. 7.250 kg of nonpareilles pellets in a coating pan are sprayed with part of the Kollidon K-30 solution until slightly humid. Then the active ingredient is added in portions until the pellets are dry. This procedure of humidification/drying is continued until all of the active ingredient mixture has been added. Then the pellets are moved around until completely dry.

After that, the pellets are filled into hard gelatine capsules (126.5 mg pellets/capsule).

Example 4

Preparation of Enteric-coated Capsules Containing 110.0 mg of Dimethyl Fumarate, which Corresponds to 88 mg of Fumaric Acid 11.000 kg of dimethyl fumarate are intensely mixed in a mixture consisting of 14.00 kg of starch, 5.65 kg of lactose, 2.00 kg of microcrystalline cellulose (Avicel®), 1.00 kg of polyvinyl pyrrolidone (Kollidon® 25) and 2.443 kg of Primogel® and, taking the necessary precautions (breathing mask, gloves, protective clothing), homogenized by means of a sieve 800.

Using a 2% aqueous solution of polyvinyl pyrrolidone (Kollidon® K25), the entire powder mixture is processed into a binder granulate in the customary manner and mixed with the outer phase when dry. Said outer phase consists of 0.350 kg of colloidal silicic acid (Aerosil®), 0.500 kg of Mg stearate and 1.500 kg of talcum. The homogenous mixture is filled into suitable capsules in portions of 400 mg which are then provided with an enteric coating consisting of hydroxy propyl methyl cellulose stearate and castor oil as plasticiser in the customary manner. Instead of using hard gelatine capsules, the product may also be filled into suitable enteric-coated capsules consisting of a mixture of cellulose acetate phthalate (CAP) and hydroxy propyl methyl cellulose phthalate (HP-MCP).

In comparison with substances of the prior art such as cyclosporine, which may cause massive kidney disorders or diseases of the lymphoproliferative system, a therapy with fumaric acid derivatives according to the invention for the indications listed above rarely results in serious side effects.

Among other things, the immunosuppressive effect of cyclosporine is caused by the inhibition of Th-1 cell formation. As in vitro experiments of the applicant have shown, fumarates cause a shift of the cytokine pattern of the Th1 type to the cytokine pattern of the Th2 type.

Especially in view of the long-term therapy and prevention which is always necessary in graft-versus-host reactions and host-versus-graft reactions or other autoimmune diseases such as multiple sclerosis, the unexpected effect of the use according to the invention is of the greatest interest. In a combination therapy of cyclosporine with the fumaric acid derivatives, the toxic side effects of the former compounds may be unexpectedly reduced to a substantial degree, In addition, the use according to the invention is also significant in the substitution of the corticosteroid therapy of autoimmune diseases which is known to be accompanied by severe side effects.

The invention claimed is:

1. A method of treating a patient in need of treatment for multiple sclerosis comprising contacting peripheral blood mono-nuclear cells or monocytes of said patient with methyl hydrogen fumarate.

2. The method of claim 1, wherein the method comprises administering to the patient an oral pharmaceutical preparation consisting essentially of dimethyl fumarate, wherein said dimethyl fumarate is converted in the body of the patient into said methyl hydrogen fumarate.

3. The method of claim 2, wherein the oral pharmaceutical preparation is formulated as a solid dosage form selected from the group consisting of micro-pellets, micro-tablets, granulates, a capsule, and a tablet.

4. The method of claim 3, wherein the solid dosage form is a tablet or capsule.

5. The method of claim 3, wherein the solid dosage form is micro-tablets.

* * * * *